United States Patent [19]
Park

[11] Patent Number: 6,133,041
[45] Date of Patent: Oct. 17, 2000

[54] HYDROGEN SULFIDE DETECTION TUBE FOR ALCOHOLIC BEVERAGES

[75] Inventor: Seung K. Park, Dept. of Food Science & Technology, Kyung Hee Univ., Kiheung-Eup, Yongin-Si, Kyungki-Do, S., Rep. of Korea

[73] Assignee: Seung K. Park, Kyungki-Do, Rep. of Korea

[21] Appl. No.: 09/182,953

[22] Filed: Oct. 29, 1998

[51] Int. Cl.[7] .................................................. G01N 31/00
[52] U.S. Cl. .............................. 436/121; 436/32; 422/80; 435/4; 435/287.5; 435/807
[58] Field of Search .............................. 435/4, 29, 287.5, 435/288.1, 300.1, 810, 807; 422/59, 68.1, 80, 61; 436/32, 120, 121, 174, 177, 808; 73/19.1

[56] References Cited

U.S. PATENT DOCUMENTS

| | | |
|---|---|---|
| 2,174,349 | 9/1939 | Littlefield . |
| 3,313,712 | 4/1967 | George . |
| 3,388,975 | 6/1968 | Wallace . |
| 3,702,235 | 11/1972 | Fallgatter . |
| 4,032,297 | 6/1977 | Lyshkow . |
| 4,083,691 | 4/1978 | McCormack et al. . |
| 4,174,202 | 11/1979 | Simpson ................................. 23/230 |
| 4,790,238 | 12/1988 | Hsu . |
| 5,062,292 | 11/1991 | Kanba et al. . |
| 5,080,867 | 1/1992 | Cooke ...................................... 422/86 |
| 5,529,841 | 6/1996 | Neihof ................................... 428/328 |

FOREIGN PATENT DOCUMENTS

| | | | |
|---|---|---|---|
| 0 202 423 A1 | 11/1986 | European Pat. Off. | ....... G01N 31/22 |
| 1310718 | 5/1987 | U.S.S.R. . | |
| 97/14781 | 4/1997 | WIPO . | |

OTHER PUBLICATIONS

"Drager–Tubes –Measuring System and Principal", Brochure of Dragonwerk, Mar. 1998, (Online Brochure).

*Primary Examiner*—William H. Beisner
*Attorney, Agent, or Firm*—David J. Weitz; Wilson Sonsini Goodrich & Rosati

[57] ABSTRACT

A kit is provided for testing a gas produced from a sample for an absolute amount of a hydrogen sulfide. The kit includes a vessel for receiving the sample to be tested. The vessel includes one or more gas flow passages through which gas within the vessel can leave the vessel. The kit also includes one or more testing tubes. Each testing tube includes a lumen through which gas can flow. The lumen includes a column of medium observable from outside the testing tube and has a length which changes in appearance in proportion to the amount of hydrogen sulfide which has passed through the testing tube. Graduations are included on the one or more testing tubes for indicating the length of the column of medium whose appearance has changed. The kit also includes a coupling mechanism for coupling the one or more testing tubes with the one or more gas flow passages such that gas leaving the vessel passes through the one or more testing tubes.

11 Claims, 9 Drawing Sheets

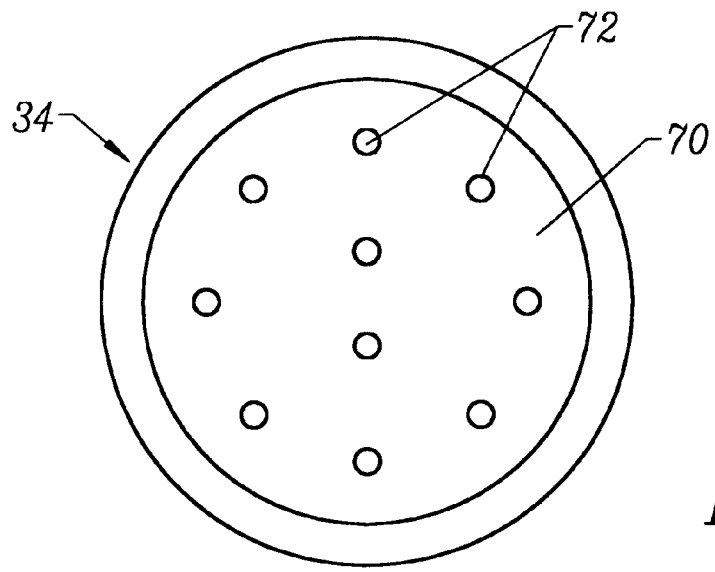
FIG. 5A
FIG. 5B
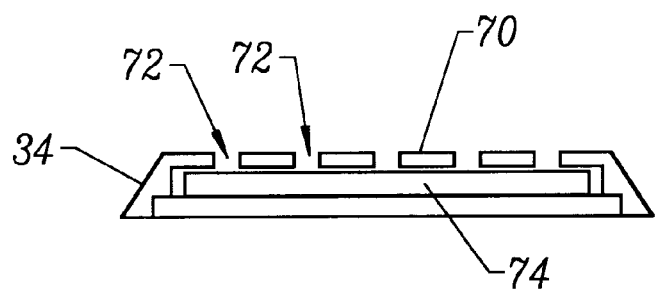
FIG. 5C
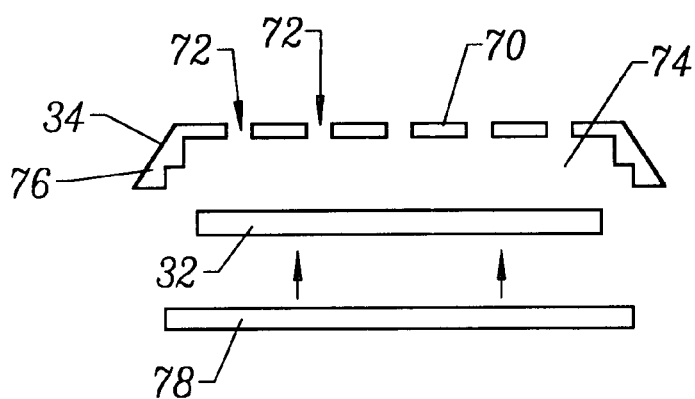
FIG. 5D

HYDROGEN SULFIDE DETECTION TUBE FOR ALCOHOLIC BEVERAGES

FIELD OF THE INVENTION

This invention relates to a kit and a method for detecting a gas evolved from a sample and, more particularly, to a kit and method for quantifying an amount of a hydrogen sulfide evolved from the sample.

BACKGROUND OF THE INVENTION

Testing samples for their ability to produce particular gasses is frequently desirable. For instance, the fermentation of alcoholic beverages such as wine and beer frequently uses yeasts which produce hydrogen sulfide. Hydrogen sulfide is of particular importance to alcoholic beverage quality for several reasons: 1) hydrogen sulfide has an aroma similar to that of rotten eggs or sewage, even when present at an extremely low level, e.g., 0.5–2 ppb in wine, 2) it is a major malodorous volatile sulfur compound produced by yeast during fermentation, 3) other volatile sulfur compounds, such as mercaptans and disulfides responsible for potent off-odor problems in wine and beer, are derived primarily from hydrogen sulfide. Hydrogen sulfide is frequently produced during fermentation at levels well above the sensory threshold and can be converted to other volatile sulfur compounds which are the cause of other off-odors, described as "burnt match", "rubber", "cooked cabbage", "onion", and "garlic". These secondary volatile sulfur compounds are extremely difficult to remove once they are formed in wine and beer. Accordingly, detection of hydrogen sulfide is important for evaluating odor formation and reducing the formation of secondary volatile sulfur compounds.

Although not used widely in wineries and breweries, instrumental analysis, such as gas chromatography with flame photometric detection, has been used in a few large breweries and wineries for the qualitative and quantitative analysis of volatile sulfur compounds. More recently, gas chromatography with sulfur chemiluminescence detection has received attention, as this analytical system allows both sensitive detection and a linear response for volatile sulfur compounds. These two analytical methods, however, require expensive instrumentation and skilled personnel to analyze volatile sulfur compounds. Very few wineries can afford these instruments for the purpose of hydrogen sulfide analysis. Moreover, analysis of hydrogen sulfide using these sophisticated instruments is time-consuming, and is complicated by unresolved problems, such as the separation of hydrogen sulfide from sulfur dioxide, another gas produced abundantly during fermentation.

A colorimetric method has also been used for detecting and quantifying hydrogen sulfide produced during alcoholic fermentation. This colorimetric test is based on the ability of hydrogen sulfide and acid-soluble metallic sulfides to convert N,N-dimethyl-p-phenylenediamine directly to methylene blue in the presence of potassium dichromate, a mild oxidizing agent. The intensity of blue color development is directly proportional to the amount of hydrogen sulfide present in the original solution. This method is relatively accurate, but it requires a time-consuming preparation and the use of a toxic solution for color development, followed by a spectrophotometric measurement. For these reasons, this method has not been used in wineries and breweries.

Color detector tube systems have been used for monitoring industrial hygiene, air pollution, and gas analysis. In this type of system, a known volume of air or gas is pulled through a glass detector with a bellows pump (a sampling pump). The tube contains a reagent which changes color in the presence of specific chemicals. The length of the colored band in the tube quantitatively indicates the concentration of the specific gas, chemical vapor or pollutant.

A need currently exists for an inexpensive, rapid, easy and reliable method and kit for detecting and quantifying the evolution of hydrogen sulfide from a sample. The method, kit and system should be sensitive enough to detect and quantify very small amounts of hydrogen sulfide.

SUMMARY OF THE INVENTION

The present invention relates to a kit for quantifying an amount of hydrogen sulfide evolved from a sample. The kit includes a vessel for housing the sample. The vessel includes one or more gas flow passages through which gas within the vessel can leave the vessel. The kit also includes one or more testing tubes. Each testing tube includes a lumen through which gas can flow. The lumen contains a medium observable from outside the testing tube. The medium changes in appearance when exposed to hydrogen sulfide. The testing tube also includes graduations for indicating a length of the medium along the lumen whose appearance has changed. The length of the medium whose appearance has changed is related to the amount of hydrogen sulfide that has passed through the testing tube. The kit also includes a coupling mechanism for coupling the one or more testing tubes with the one or more gas flow passages such that substantially all the gas evolved from the sample passes through the one or more testing tubes.

The present invention also relates to a method for quantifying an amount of hydrogen sulfide evolved from a sample. According to the method, a sample is placed within a vessel having one or more gas flow passages coupled with one or more testing tubes such that substantially all gas leaving the vessel passes through the one or more testing tubes. Each testing tube includes a lumen through which gas can flow. The lumen contains a medium observable from outside the testing tube. The medium changes in appearance when exposed to hydrogen sulfide. Gas for extracting hydrogen sulfide from the sample is caused to be expelled from the vessel through the one or more testing tubes. The amount of hydrogen sulfide in the expelled gas is quantified based on the length of the medium which changes in appearance.

The invention also relates to a method for quantifying an amount of hydrogen sulfide evolved from a sample during a fermentation. According to the method, the sample is placed within a vessel having one or more gas flow passages coupled with one or more testing tubes such that substantially all gas leaving the vessel passes through the one or more testing tubes. Each testing tube includes a lumen through which gas can flow. The lumen contains a medium observable from outside the testing tube. The medium changes in appearance when exposed to hydrogen sulfide. The sample is then fermented within the vessel, the fermentation producing a gas which is expelled from the vessel through the one or more testing tubes. After a period of time, an amount of hydrogen sulfide expelled from the vessel is quantified based on a length of the medium which has changed in appearance.

BRIEF DESCRIPTION OF THE FIGURES

FIG. 2A illustrates positioning a testing tube within a channel in a coupling mechanism.

FIG. 2B illustrates delivering a sample into a vessel.

FIG. 2C illustrates positioning a gas sample container within a vessel.

FIG. 2D illustrates positioning the coupling mechanism within a gas flow passage in a vessel.

FIG. 2E illustrates reading a testing tube which has been exposed to hydrogen sulfide.

FIG. 4A illustrates an end of a testing tube coupled with a sealing structure which has gripping sections in contact with the inside of a testing tube.

FIG. 4B illustrates an end of a testing tube coupled with a sealing structure which has gripping sections in contact with the inside of a testing tube.

FIG. 4C illustrates an end of a testing tube coupled with a sealing structure which has gripping sections in contact with the outside of a testing tube.

FIG. 4D illustrates an end of a testing tube coupled with a sealing structure which has gripping sections in contact with the outside of a testing tube.

FIG. 4E illustrates sealing structures being removed from a testing tube.

FIG. 5A provides a perspective view of a gas source which is a tablet.

FIG. 5B provides a topview of an embodiment of a gas source container.

FIG. 5C provides a cross sectional view of the gas source container illustrated in FIG. 5B.

FIG. 5D provides a cross sectional view of a two part gas source container.

DETAILED DESCRIPTION OF THE PREFERRED EMBODIMENT

Figure 1:
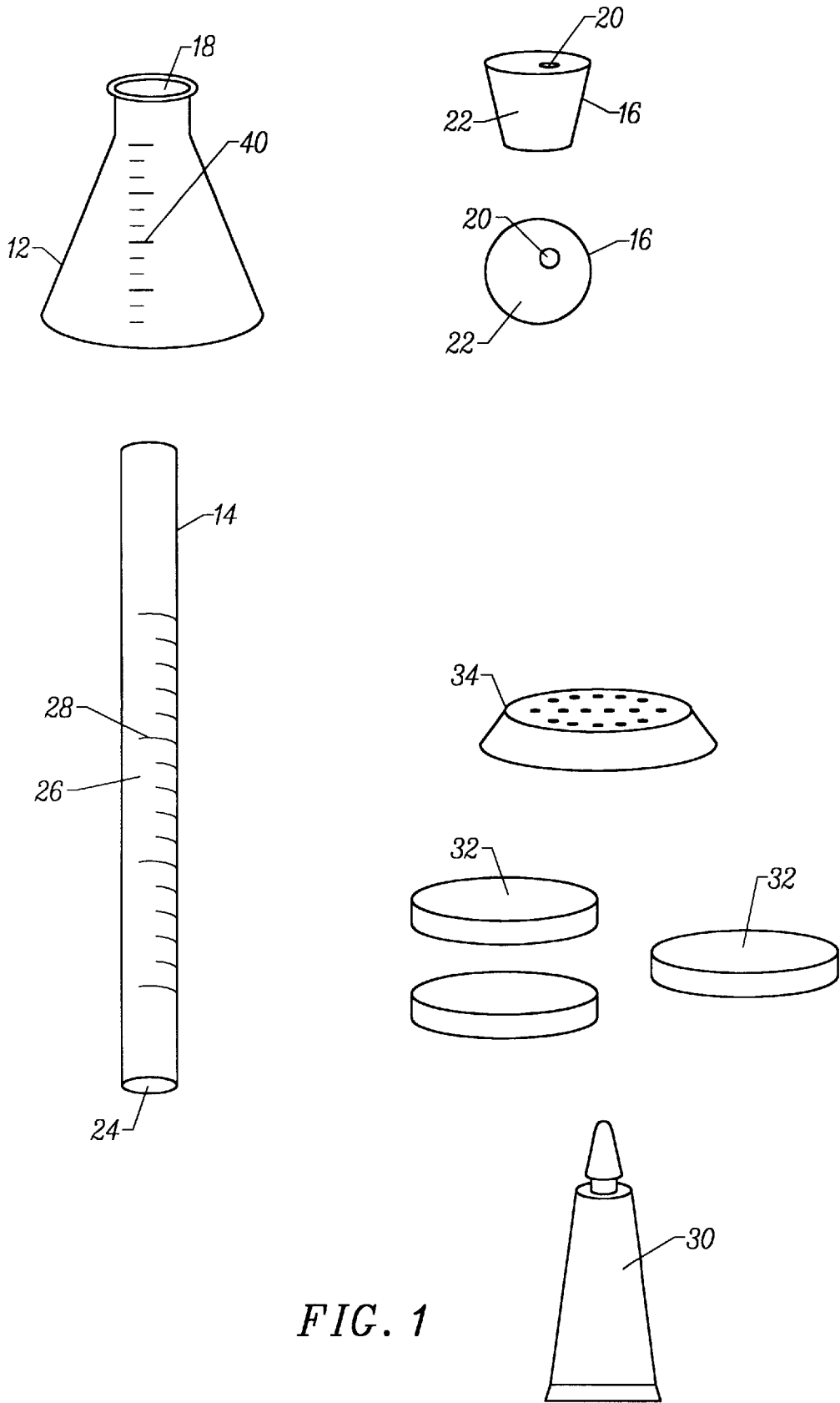
FIG. 1 illustrates an embodiment of a kit according to the present invention.

The present invention relates to a kit and method for quantifying an amount of hydrogen sulfide evolved from a sample. The kit includes a vessel for housing the sample. The vessel has one or more gas flow passages through which gas within the vessel can leave the vessel. Suitable vessels for use with the kit include, but are not limited to, an Erlenmeyer flask. The kit also includes one or more testing tubes which include lumens through which a gas can flow. The testing tubes can be coupled with the vessel such that substantially all the gas evolved from the sample within the vessel passes through the lumens in the one or more testing tubes.

The lumen in each testing tube contains a medium which changes in appearance upon exposure of the medium to hydrogen sulfide within the gas passing from the vessel through the lumen. The change in the appearance of the medium can be observed from outside the testing tube. Each testing tube also includes graduations for indicating the length of the medium which has changed in appearance. The length of the medium which has changed appearance relates to the quantity of hydrogen sulfide to which the medium has been exposed. As a result, there is a relationship between the length of the medium which has changed appearance and the quantity of hydrogen sulfide which has passed through the lumen. This relationship is used to calibrate the graduations such that at least a portion of the graduations are correlated with a number. The number indicates the quantity of hydrogen sulfide which has passed through the lumen when the changed length of the medium has reached the graduation. As a result, the testing tubes can be used to quantify the amount of hydrogen sulfide which has evolved from the sample and passed through the lumen.

The ability to quantify the amount of hydrogen sulfide which has passed through the testing tube is an important feature of the present invention. This value allows the quantity of hydrogen sulfide per mass of sample or per volume of sample to be determined and avoids the need to calculate the total amount of all gasses which passed through the lumen in the testing tube. The quantity of hydrogen sulfide per mass of sample or per volume of sample allows different samples to be compared for their hydrogen sulfide content or for their capacity to produce hydrogen sulfide.

The sample can include a liquid such as wine or beer. Since hydrogen sulfide is volatile within a liquid, a liquid containing hydrogen sulfide will release a volume of hydrogen sulfide gas over time. The amount of hydrogen sulfide evolved by a liquid sample is a function of the hydrogen sulfide content of the liquid. As a result, the hydrogen sulfide contents of various liquids can be compared.

The sample can also include solids such as soil. The sample can also include a combination of liquid and solid. For instance, liquid can be added to a solid in order to dissolve the solid entirely or to dissolve any hydrogen sulfide precursors within the solid. The amount of hydrogen sulfide evolved from the sample can then be examined to determine its hydrogen sulfide evolving characteristics. As a result, different solid samples can be studied for their hydrogen sulfide evolving characteristics.

The sample can also be fermented within the vessel to examine the amount of hydrogen sulfide evolved during a fermentation. The amount of hydrogen sulfide evolved during a fermentation can vary depending on the strain of yeast used in the fermentation. As a result, the hydrogen sulfide producing characteristics of different yeast strains can be studied using the present invention. Much of the hydrogen sulfide produced during a fermentation is evolved during the first two or three days after the onset of the fermentation. This early evolution of hydrogen sulfide allows the results for different samples to be compared at early stages of fermentation. The early comparison reduces the need to carry out long fermentations in order to compare results. Accordingly, the best yeast for fermenting a particular liquid can be quickly identified.

According to the method, a gas can be delivered into the vessel. The additional gas serves to drives gas from within the vessel through the lumen in the testing tube. The gas can be delivered from a gas source which is external to the vessel or from a gas source which is internal within the vessel. The additional gas may be delivered into the sample or into the headspace above the sample. In either event, the additional gas drives gas from the headspace reduces the partial pressure of the hydrogen sulfide within the headspace. The reduced partial pressure causes more hydrogen sulfide to be evolved from the sample. As a result, substantially all the hydrogen sulfide can be removed from the sample. Suitable gasses for delivery into the head space include, but are not limited to, carbon dioxide. The volume of gas delivered into the vessel is preferably larger than the volume of the vessel, more preferably at least twice as large as the volume of the vessel and most preferably at least three times as large as the volume of the vessel.

FIG. 1 illustrates a kit according to the present invention. The kit includes a vessel 12 for receiving a sample, a testing tube 14 and a coupling mechanism 16 for coupling the testing tube 14 with the vessel 12. The vessel 12 includes one or more gas flow passages 18. Suitable vessels 12 include, but are not limited to, a flask. The coupling mechanism 16 can be a stopper including one or more channels 20 bored through the coupling mechanism body 22. The channel 20 is sized to receive the testing tube 14. The testing tube 14 can include a lumen 24 which contains a medium 26 which can be observed through the testing tube 14. The medium 26 changes in appearance upon exposure to hydrogen sulfide. Graduations 28 are included on the testing tube 14. The graduations 28 can be compared against the degree of change in the medium 26 to determine the quantity of hydrogen sulfide which has passed through the lumen 24 in the testing tube 14.

The kit can also optionally include a lubricant container 30. The lubricant container 30 contains a lubricant which can be used to aid in positioning the testing tube 14 within the channel 20 of the coupling mechanism 16. Suitable lubricants include, but are not limited to, a petroleum jelly such as Vaseline and beeswax. The kit can also optionally include one or more gas sources 32 and a gas source container 34. The gas source 32 illustrated in FIG. 1A is a tablet such as a sodium bicarbonate tablet or ALKASELTZER, however, as will be discussed in more detail, other gas sources 32 can be used.

Figure 2A:
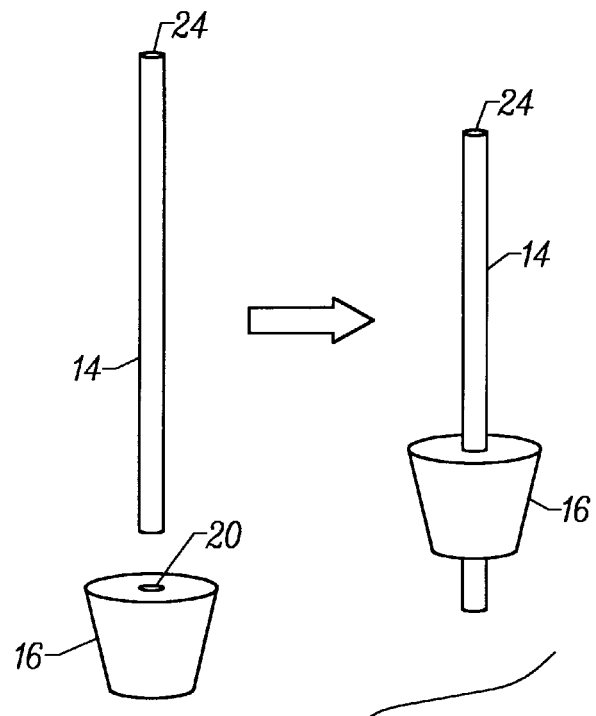
FIGS. 2A–2E illustrate a method for quantifying an amount of hydrogen sulfide evolved from a sample.
Figure 2B:
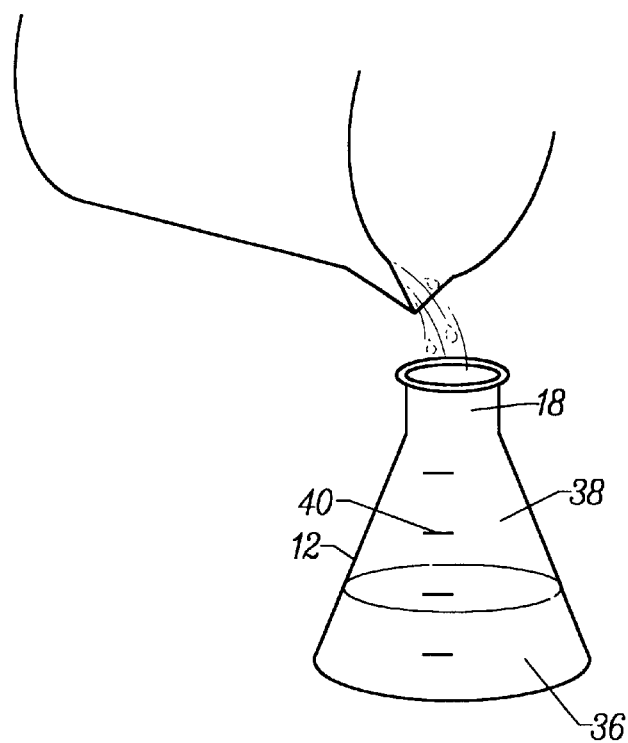

FIGS. 2A–2E illustrate a method of operating the kit. FIG. 2A illustrates the testing tube 14 being positioned within the channel 20 of the coupling mechanism 16. The optional lubricant can be applied to an outer surface of the testing tube 14 and/or the channel 20 before the testing tube 14 is positioned within the channel 20. In FIG. 2A, the testing tube 14 is illustrated as extending completely through the channel 20 in the coupling mechanism 16. However, the testing tube 14 can be partially inserted into the channel 20 in the coupling mechanism 16. In one embodiment of the kit, the testing tube 14 and the coupling mechanism 16 are integral and the step illustrated in FIG. 2A is eliminated. FIG. 2B illustrates a sample 36 being delivered into the vessel 12. The vessel includes graduations 40 which can be used to indicate to the user the volume of the sample delivered into the vessel or to assure that a consistent amount of sample is used when each sample is delivered into the vessel. Although the sample 36 illustrated is a fluid, the sample 36 can also be a solid or a combination of solid and liquid (e.g. a solution, suspension or emulsion).

Figure 2C:
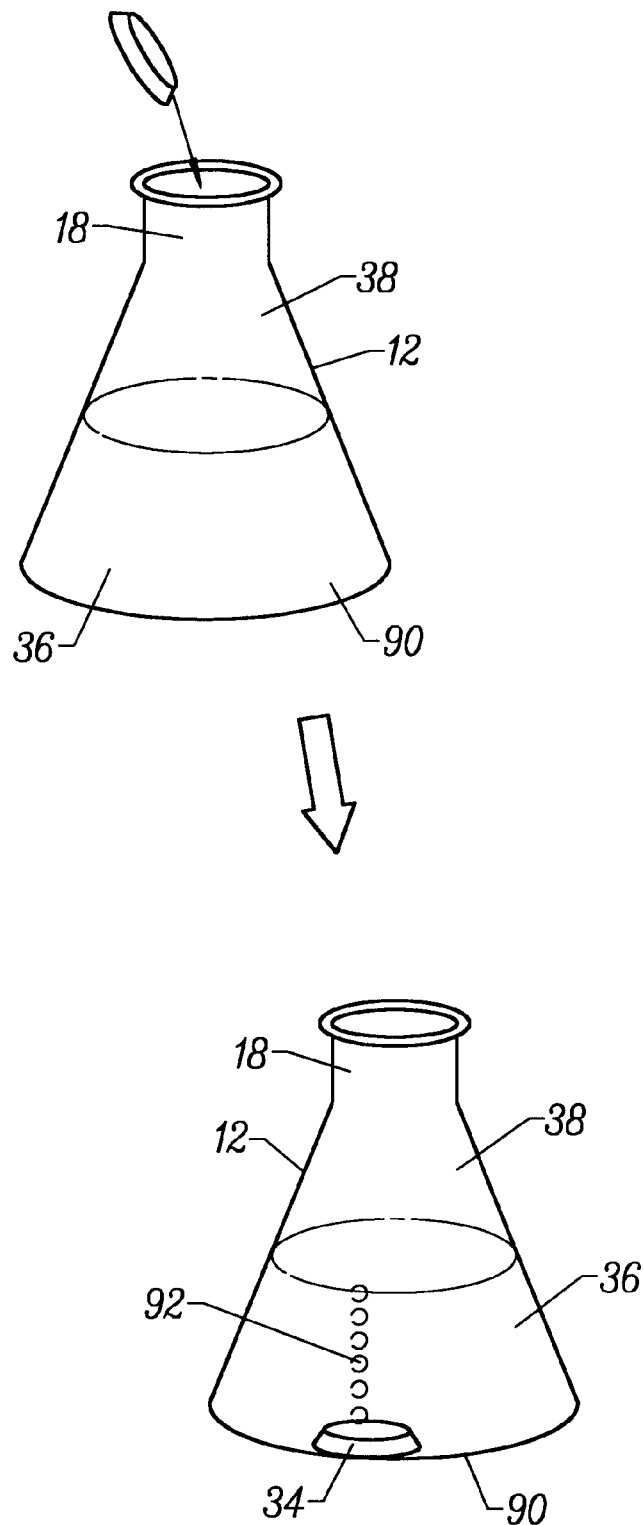

FIG. 2C illustrates a gas source container 34 being delivered into the vessel 12 via the gas flow passage 18. The gas source container 34 is weighted such that the gas source container 34 sits on the bottom 90 of the vessel 12. A gas is produced from the gas source 32 within the gas source container 34.

Figures 2D, 2E:
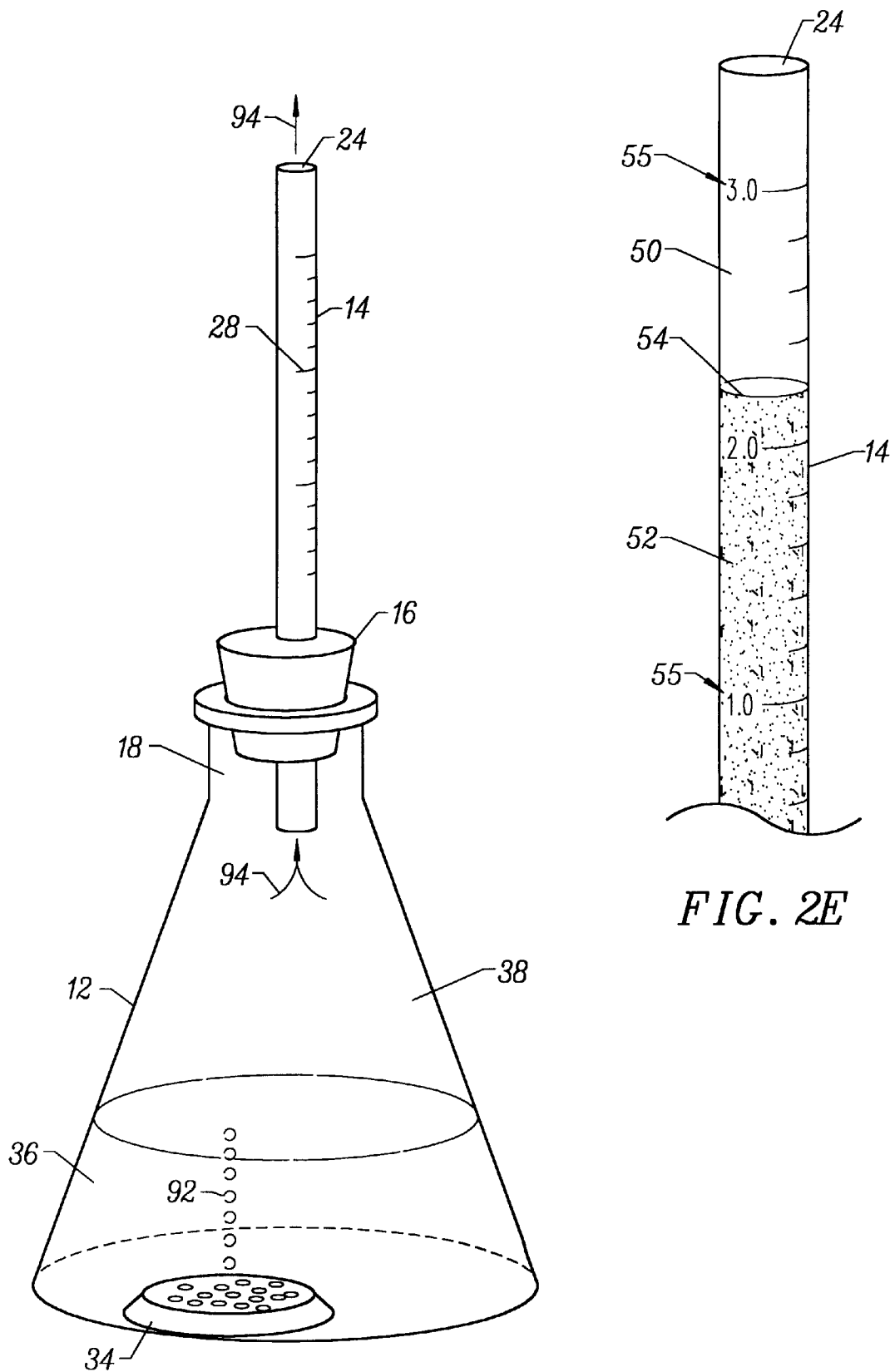

FIG. 2D illustrates the coupling mechanism 16 coupling the testing tube 14 with the vessel 12. The gas bubbles 92 up through the sample 36 and fills the head space 38 in the vessel 12, thereby creating a pressure gradient across the lumen 24 in the testing tube 14. The pressure gradient drives the gasses within the head space 38 through the lumen 24 in the testing tube 14 as illustrated by the arrows 94. Since hydrogen sulfide is known to be a volatile gas, hydrogen sulfide is frequently present within the head gas and also passes through the lumen 24 where it contacts the medium 26. As described above, reducing the partial pressure of the hydrogen sulfide in the head space causes the sample to evolve additional hydrogen sulfide. Continuous delivery of a gas into the vessel can cause substantially all the hydrogen sulfide within a sample to be evolved from the sample.

FIG. 2E illustrates the change in the medium 26 on exposure to hydrogen sulfide. A portion of the medium 26 remains unchanged 50 while a black band 52 is formed in the portion of the medium 26 which was exposed to sufficient hydrogen sulfide to change the color of the medium 26. The graduations 28 can be read by comparing the graduations 28 against the position of the line 54 in the medium 26. For instance, the medium 26 illustrated in FIG. 2E has been exposed to 2.2 $\mu$g of hydrogen sulfide.

The steps illustrated in FIGS. 2A–2E can be varied. For instance, the gas source container 34 can be added to the vessel 12 before the sample 36, after the sample 36 or intermittently with different portions of the sample 36. The gas source container 34 can be eliminated and replaced with the gas source 32 embodiments illustrated in FIGS. 6A–6B. Further, the gas source 32 can be entirely eliminated. For instance, the sample 36 can be fermented within the vessel 12. The fermentation process can produce enough gas that the measurement from the sampling tube 14 can be sufficient without a gas source 32. In addition, as will be discussed below, the kit can be designed so a gas can be delivered into the vessel from a gas source which is external to the vessel.

Figure 3A:
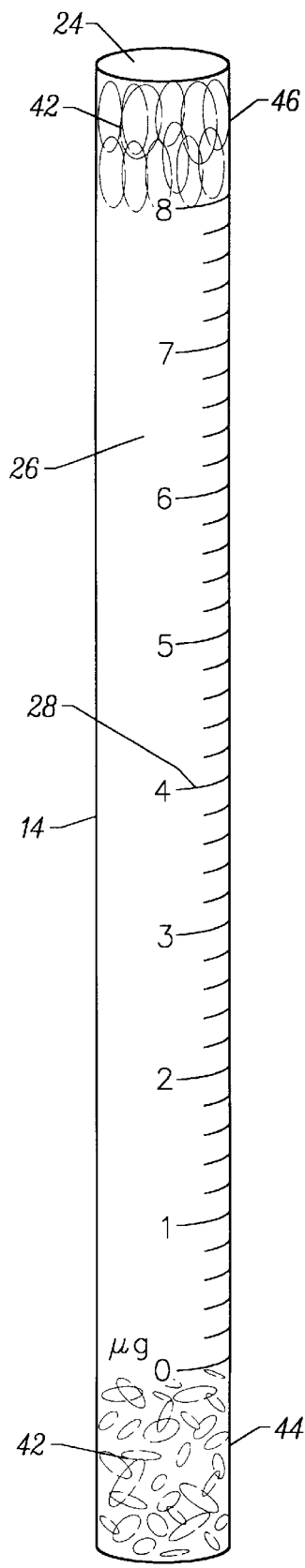
FIG. 3A illustrates a testing tube before it has been exposed to hydrogen sulfide.

FIG. 3 illustrates a testing tube 14. The testing tube 14 is preferably constructed from a transparent material such as glass or plastic. The lumen 24 within the testing tube 14 contains a medium 26 and fillers 42 positioned at a first end 44 and a second end 46 of the testing tube 14. The fillers 42 are preferably constructed from porous materials which does not substantially impede the flow of gasses through the lumen. Suitable filler materials include, but are not limited to, cotton or porous plastic.

The medium 26 includes a support impregnated with an impregnation material. Suitable impregnation materials include, but are not limited to, metal acetates and other materials which change color upon exposure to hydrogen sulfide. Suitable metal acetates include, but are not limited to, bismuth, lead, silver, and zinc. Preferred among these are lead and silver, with lead being the most preferred due to stability and expense. Cationic lead readily forms complexes with anionic ligands, such as sulfhydryl groups, resulting in the formation of insoluble lead sulfide, which is black in color. Lead acetate has been widely used in hair coloring, and regulatory approval has been granted in various countries including the USA, Australia, Brazil, Canada, many Asian countries, and the European Community (EEC, 1990). In the USA, the FDA (1980 and 1981) concluded that lead acetate was safe for use in cosmetics that color the hair of the scalp, and approved its use, subject to a maximum content of 0.6% (w/v) lead in the product.

Suitable supports can be impregnated with the impregnation materials. Suitable supports include, but are not limited to, Diatomite silica supports. These diatomite supports are readily available from various manufacturers, and are produced by calcination of diatomite or its fractions with alkali additives (2–5%). These supports are white in color, have a pH of 8–10, and a pore size of 8–10 $\mu$m. They have a homogeneous porous structure with a small specific surface (about 1 m²/g), a relatively low specific adsorptive activity, and are catalytically inert. The surface of the untreated (original) support possesses strongly pronounced alkaline properties (pH about 8–10). The diatomite supports themselves do not show any color change upon reaction with hydrogen sulfide, but impregnation with a known concentration of lead acetate affords a color change from white to black upon reaction with hydrogen sulfide. The diatomite supports are impregnated with lead acetate by using a technique known as rotary vacuum evaporation or fluidized bed drying method. A typical ratio of diatomite supports (typically, 60–120 mesh) and lead acetate is as follows: 100 grams of diatomite supports are mixed with about 400 mL of 2.5% lead acetate in alcohol (other solid support materials will have a different ratio). The mixed solution is "allowed to stand for half an hour, and then is dried under reduced pressure, using a rotary vacuum evaporator to effect homogenous and low temperature drying.

The size of the diatomite supports and the concentration of lead acetate solution can be varied depending on the volume of the sample 36 being tested. Similarly, the size of the testing tube 14 is varied depending on the volume of the sample 36 being tested. For example, a testing tube 14 used for 100–300 mL of sample 36 in a 500 mL vessel 12 would be about 120 mm long, with an inside diameter of about 3 mm. About 70–80% of the length would filled with the quantifying media. For a larger volume of sample 36, the size of the testing tube 14 used would be bigger.

The size of the testing tube 14 can be varied depending on the type of fermentation (e.g. wine, beer, or whiskey) and the volume of the sample 36. For instance, smaller diameter testing tubes 14 should be used with samples 36 which produce smaller quantities of hydrogen sulfide. The smaller diameter testing tube 14 will cause the graduations to be expanded to provide an increased sensitivity to the hydrogen sulfide.

Figure 3B:
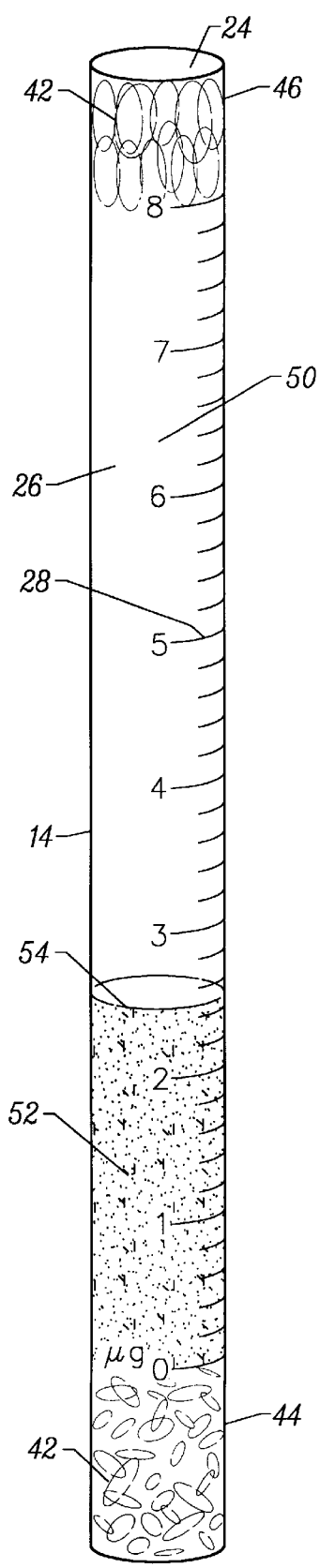
FIG. 3B illustrates a testing tube after it has been exposed to hydrogen sulfide.

FIG. 3B illustrates a testing tube 14 with a medium 26 which has been exposed to hydrogen sulfide. A portion of the medium 26 remains unchanged 50 while a black band 52 is formed in the portion of the medium 26 which was exposed to sufficient hydrogen sulfide to change the color of the medium 26. A line 54 is defined at the intersection of the black band 52 and the unchanged 50 medium 26. There is a relationship between the length of the medium 26 which has changed appearance and the quantity of hydrogen sulfide which has passed through the lumen. As will be discussed below, this relationship is used to calibrate the graduations 28 such that at least a portion of the graduations 28 are correlated with a number 55. The number 55 indicates the quantity of hydrogen sulfide which has passed through the lumen when the line 54 has reached a particular graduation. As a result, the quantity of hydrogen sulfide which has passed through the lumen can be determined by comparing the graduations 28 against the position of the line 54 in the medium 26. For instance, the medium 26 illustrated in FIG. 3B has been exposed to 2.4 μg of hydrogen sulfide.

The testing tubes 14 are calibrated to determine a relationship between the length of the black band 52 and the amount of hydrogen sulfide which has passed through the lumen 24 in the testing tube 14. The calibration can be performed by exposing the testing tube 14 to known volumes of a diluted standard hydrogen sulfide gas. Table 1 illustrates the results for calibration of a testing tube 14 having a length of 120 mm and an inner diameter of 3 mm. Table 2 illustrates the results for a testing tube 14 having a length of 200 mm and an inner diameter of 6 mm. Table 1 illustrates that a testing tube 14 with a 3 mm inner diameter can detect hydrogen sulfide quantities on the order of 0.1 μgs which is approximately the amount of hydrogen sulfide produced from a 300 ml sample 36 of finished wine with a hydrogen sulfide concentration or 0.3 ppb. Further, Table 1 in combination with Table 2 illustrates that decreasing the inner diameter of the testing tube 14 increases the sensitivity to lower levels of hydrogen sulfide.

TABLE 1

Repeated Detection and Calibration Test No. I (* SD ± 5%)

| Total hydrogen sulfide ($\mu$g, $10^{-6}$g) | Blackened distance in the tube (mm)* | Total hydrogen sulfide ($\mu$g, $10^{-6}$g) | Blackened distance in the tube (mm)* |
|---|---|---|---|
| 0.09 | 0.1 | 19.05 | 22.5 |
| 0.46 | 0.5 | 25.40 | 30.0 |
| 1.37 | 1.5 | 31.75 | 37.5 |
| 2.54 | 3.0 | 38.10 | 45.0 |
| 3.81 | 4.5 | 44.45 | 52.5 |
| 5.08 | 6.0 | 50.80 | 60.0 |
| 6.53 | 7.5 | 57.15 | 67.5 |
| 9.53 | 13.0 | 63.50 | 75.0 |
| 12.70 | 15.0 | 76.20 | 90.0 |
| 15.87 | 18.8 | 88.90 | 105.0 |
| 101.60 | 16.0 | | |

TABLE 2

Repeated Detection and Calibration Test No. II (* SD ± 5%)

| Total hydrogen sulfide ($\mu$g, $10^{-6}$g) | Blackened distance in the tube (mm)* | Total hydrogen sulfide ($\mu$g, $10^{-6}$g) | Blackened distance in the tube (mm)* |
|---|---|---|---|
| 3.04 | 0.4 | 242.88 | 32.0 |
| 6.08 | 0.8 | 273.24 | 36.0 |
| 9.09 | 1.2 | 303.60 | 40.0 |
| 12.16 | 1.6 | 333.96 | 44.0 |
| 15.18 | 2.0 | 364.32 | 48.0 |
| 22.80 | 3.0 | 394.68 | 52.0 |
| 30.36 | 4.0 | 425.04 | 56.0 |
| 37.95 | 5.0 | 455.40 | 60.0 |
| 45.54 | 6.0 | 485.76 | 64.0 |
| 60.72 | 8.0 | 516.12 | 68.0 |
| 75.90 | 10.0 | 546.48 | 72.0 |
| 91.08 | 12.0 | 576.84 | 76.0 |
| 106.26 | 14.0 | 607.20 | 80.0 |
| 121.44 | 16.0 | 637.56 | 84.0 |
| 136.62 | 18.0 | 667.92 | 88.0 |
| 151.80 | 20.0 | 698.36 | 92.0 |
| 182.16 | 24.0 | 759.00 | 100.0 |
| 197.34 | 26.0 | | |
| 212.52 | 28.0 | | |

The graduations can be positioned on the testing tubes according to these calibration tables. For instance, given a testing tube with a lumen diameter which matches the lumen diameter of the testing tube used to create these tables, the graduations can be positioned on the testing tubes such that the medium between two adjacent graduations changes in appearance when exposed to particular amounts of hydrogen sulfide. For instance, the graduations can be positioned such that the medium between adjacent graduations preferably changes in appearance when exposed to 0.4 μg hydrogen sulfide, more preferably 0.2 μg hydrogen sulfide and most preferably 0.1 μg of hydrogen sulfide. The graduations can also be positioned on the testing tube such that the quantity of hydrogen sulfide which has passed through the lumen can be measured to within about 5% and more preferably within about 2%.

Figure 4A:
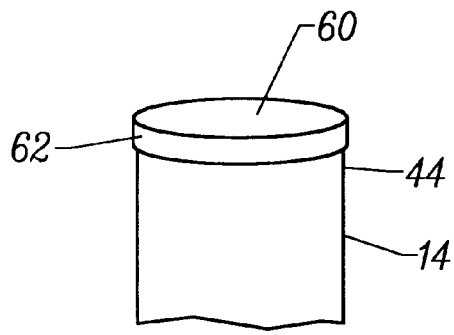
FIGS. 4A–4E illustrate methods for coupling and decoupling sealing structures with a testing tube.
Figure 4C:
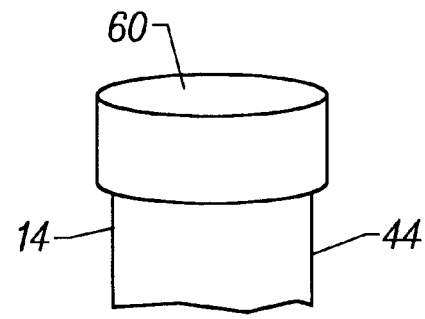
Figure 4B:
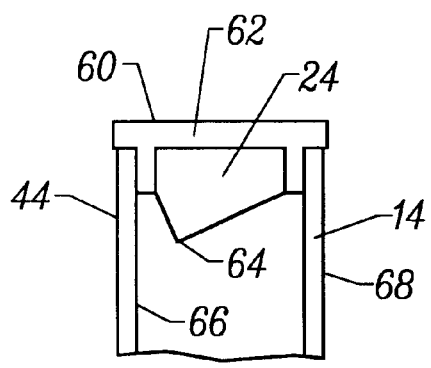
Figure 4D:
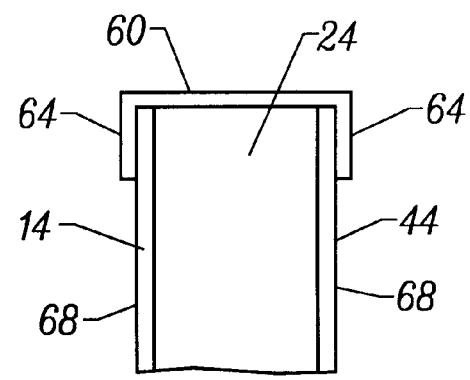

As illustrated in FIGS. 4A–4D, the first end 44 and the second end 46 of the testing tube 14 can be coupled with a sealing structure 60. The sealing structure can serve as a temporary cap which keep the contents of the tube stable during storage and handling. As illustrated in FIGS. 4A and 4B, the sealing structure 60 can include a flange 62 and a gripping section 64. The gripping section 64 can be in contact with the inside 66 of the testing tube 14 as illustrated in FIG. 4B and the flange 62 can serve to prevent the sealing structure 60 from being pushed into the testing tube 14. As illustrated in FIG. 4D, the gripping sections 64 can contact the outside 68 of the testing tube 14.

Figure 4E:
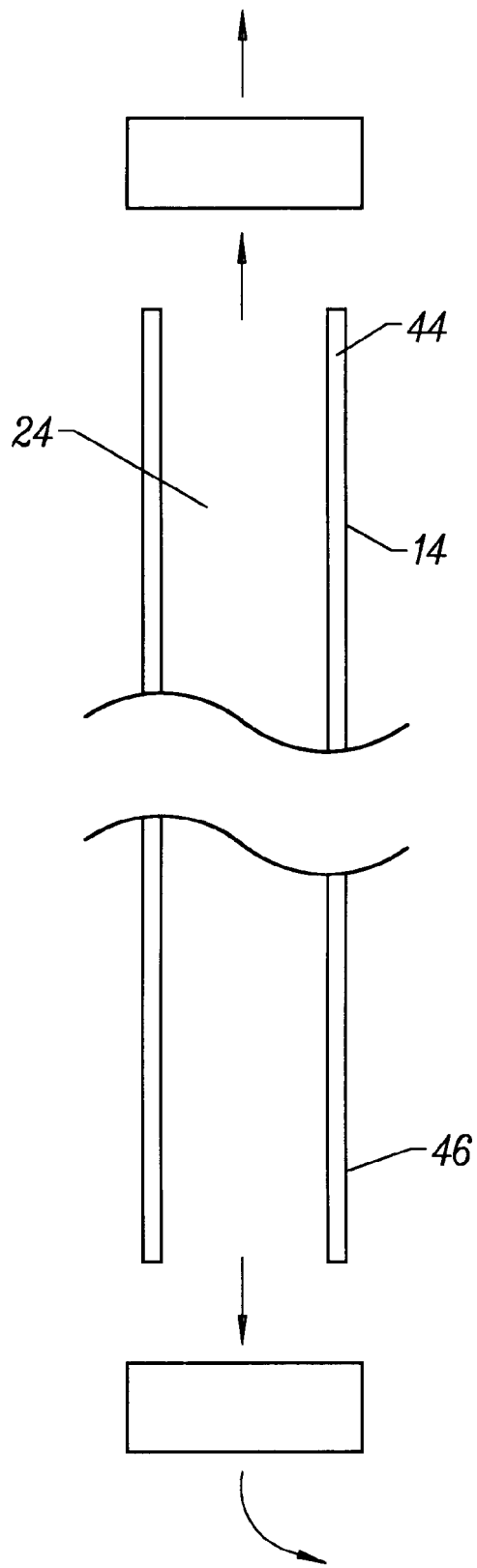

The friction between the testing tube 14 and the gripping section 64 should be sufficient to keep the sealing structures 60 in place during normal transportation and handling of the testing tubes 14, however, the sealing structure 60 should be manually detachable from the testing tube 14 as illustrated in FIG. 4E. The detachment of the scaling structure from the testing tube can occur before or after the testing tube is positioned within the channel in the coupling mechanism. Suitable materials for the sealing structures 60 include, but is not limited to, soft plastics and/or waxes.

FIGS. 5A–5D illustrates one embodiment of a gas source 32 and a gas source container 34. As illustrated in FIG. 5A, the gas source 32 can be a tablet which will produce a gas when included in the vessel 12 with a sample 36. For instance, when the sample 36 is an aqueous based solution, the gas source can be a sodium bicarbonate tablet which dissolves in water to produce carbon dioxide. Suitable gasses for use with the present invention are gasses which can be used to drive the gas within the head space 38 of the vessel 12 through the lumen 24 in the testing tube 14.

FIG. 5B illustrates a top side 70 of a gas source container 34. The top side 70 includes a plurality of openings 72. The openings 72 are sized such that the fluid within the sample 36 can flow through the openings 72 and that gas produced by the gas source 32 can flow through the openings 72. FIG. 5C is a cross section of the gas source container 34. The gas source 32 is positioned within a gas source chamber 74. The fluid from the sample 36 which flows through the openings 72 contacts the gas source 32 and can dissolve the gas source 32. As described above, the dissolution of the gas source 32 produces a gas. As illustrated in FIG. 5D, the gas source 32 can include an upper section 76 which is detachable from a lower section 78. As a result, the gas source container 34 can be used with more than one gas source 32. The gas source container 34 can be weighted so the gas source 32 remains in position on the bottom of the vessel 12. Further, the openings 72 can have a size, shape and density which decreases the exposure of the gas source 32 to the sample 36. As a result, the gas source container 34 can slow the rate of dissolution of the gas source 32.

Figure 6A:
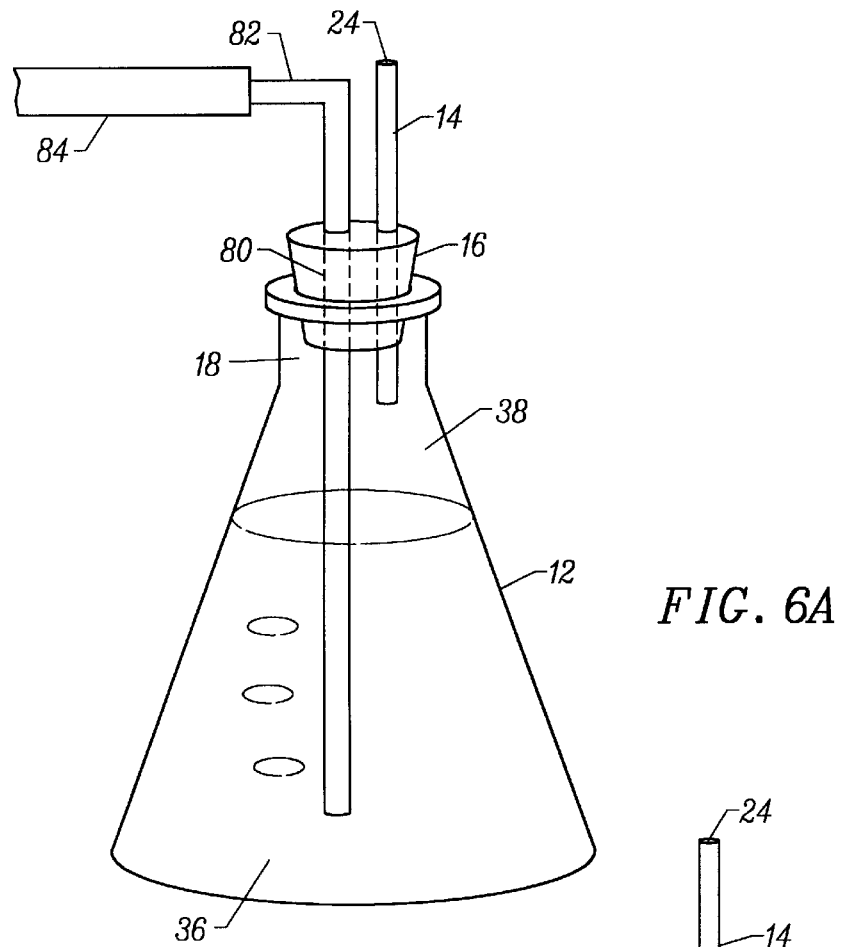
FIG. 6A is a sideview of a vessel where a gas from an external gas source is delivered into the vessel via a second channel within a coupling mechanism.

FIG. 6A illustrates another method for delivery of gas into the head vessel. The coupling mechanism 16 includes a second channel 80. A gas source fixture 82 can be received within the second channel 80. The gas source fixture 82 can be coupled with tubing 84 which is in turn coupled to a gas source 32 which is typically included in many laboratory settings (not shown). For instance, typical gas sources include tanks containing compressed air, nitrogen or carbon dioxide. The gas source fixture 82 and the tubing 84 can be included with the kit according to the present invention. As illustrated, the gas source fixture 82 can extend from the coupling mechanism 16 and into the sample 36. This configuration allows the gas bubbles 92 up through the sample 36, however, the gas can be delivered directly into the head space 38 of the vessel 12.

Figure 6B:
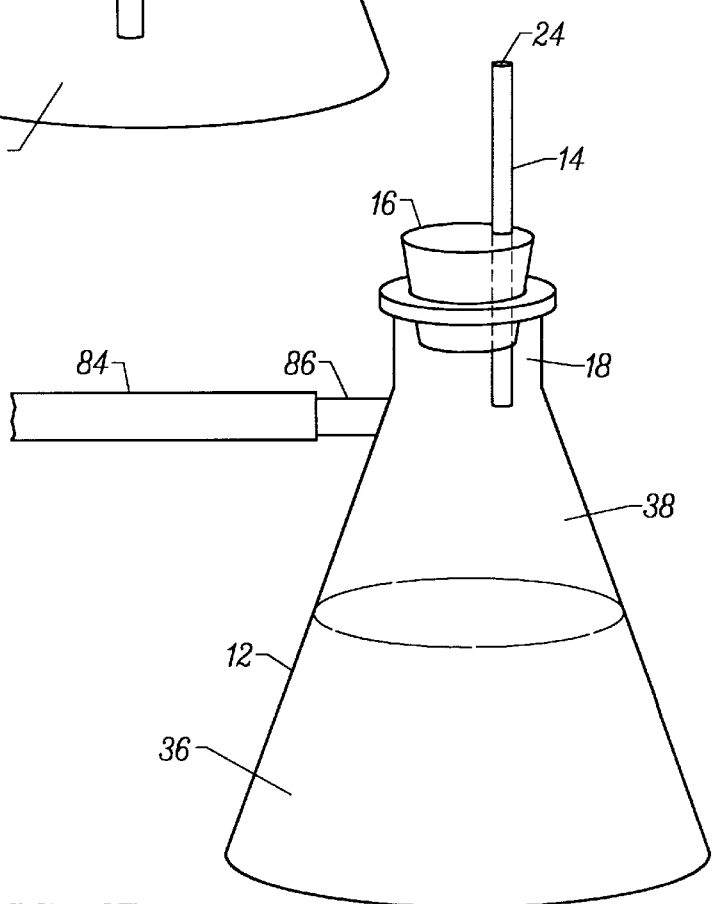
FIG. 6B is a sideview of a vessel where a gas from an external gas source is delivered into the vessel via a second gas flow channel included in the vessel.

FIG. 6B illustrates yet another method for delivery of gas into the head space. The vessel 12 includes a second gas flow passage 86 coupled with tubing 84. The tubing 84 can be coupled with a gas source 32 which is typically included in many laboratory settings (not shown). The tubing 84 can be included with the kit according to the present invention. As illustrated the second gas flow passage 86 does not contact the sample 36, however, the vessel 12 can be constructed so the second gas flow passage 86 has sufficient length to extend into the sample 36.

The kit can be used to determine the amount of hydrogen sulfide evolved during fermentation of a liquid such as wine or beer. For instance, Table 3 illustrates the hydrogen sulfide evolved during fermentation of several 100 ml samples 36 of grape juice with different amounts of elemental sulfur dissolved in them.

TABLE 3

| Blackened band in the tube (mm) | Elemental sulfur (mg/L) | Total hydrogen sulfide ($\mu$g, $10^{-6}$g) |
| --- | --- | --- |
| 0.0 | 0 | 0.00 |
| 0.5 | 10 | 0.46 |
| 1.0 | 20 | 0.92 |
| 1.5 | 30 | 1.37 |
| 2.0 | 40 | 1.80 |
| 2.5 | 50 | 2.12 |
| 3.0 | 60 | 2.54 |

The kit can also be used to test different yeast strains for their capacity to evolve hydrogen sulfide during the fermentation process. Table 4 illustrates the results for fermenting 100 ml samples 36 of grape juice with two different types of yeast. As illustrated, the Premier Cuvee consistently produced less hydrogen sulfide during each fermentation. As a result, the Premier Cuvee would be the preferable yeast for fermenting beverages. During the experiments used to develop Table 4, most of the hydrogen sulfide evolved during the first two or three days of the onset of fermentation. As a result, the fermentation need not be carried to completion in order for the yeast samples to be compared.

TABLE 4

| | Total length of the blackened band in the tube (mm) | |
| --- | --- | --- |
| | S. Cerevisiae Montrachet | Premier Cuvee |
| Wettable sulfur | | |
| 0 mg/L | 1.3 | 0.3 |
| 5 mg/L | 2.7 | 0.8 |
| 15 mg/L | 10.0 | 2.1 |
| Dusting sulfur | | |
| 5 mg/L | 4.0 | 0.4 |
| 15 mg/L | 15.1 | 1.8 |

The kit can also be used to determine the hydrogen sulfide content of a sample which was previously fermented. Table 5 illustrates the results for two finished wines. A testing tube 14 with a length of 120 mm and an inner diameter of 3 mm was used to develop the data illustrated in Table 5. An ALKASELTZER® tablet was used as the gas source 32. The hydrogen sulfide content is listed as a concentration of hydrogen sulfide within the wine. As described above, delivering a sufficient amount of gas into the head space for a sufficient time can evolve substantially all the hydrogen sulfide from the sample. As a result, the hydrogen sulfide content of the sample can be determined by dividing the amount of hydrogen sulfide evolved from the sample by the volume of the sample.

TABLE 5

|  | Red wine H$_2$S content | White wine H$_2$S |
|---|---|---|
| Hydrogen sulfide | 2 ppb | 17 ppb |

While the present invention is disclosed by reference to the preferred embodiments and examples detailed above, it is to be understood that these examples are intended in an illustrative rather than limiting sense, as it is contemplated that modifications will readily occur to those skilled in the art, which modifications will be within the spirit of the invention and the scope of the appended claims.

What is claimed is:

1. A method for quantifying an amount of hydrogen sulfide evolved from a sample during a reaction, comprising:

placing the sample within a vessel having one or more gas flow passages coupled with one or more testing tubes such that substantially all gas leaving the vessel passes through the one or more testing tube, each testing tube including a lumen through which gas can flow, the lumen containing a medium observable from outside the testing tube, the medium changing in appearance when exposed to hydrogen sulfide such that the amount of hydrogen sulfide evolved from the sample over a period of time is quantified by an amount of the medium whose appearance is changed;

causing a reaction which produces hydrogen sulfide to occur within the sample to produce a gas to be expelled from the vessel through the one or more testing tubes, such that substantially all the hydrogen sulfide evolved from the sample is absorbed in the medium within the one or more testing tubes; and quantifying an amount of hydrogen sulfide produced from the sample based on the amount of the medium which has changed in appearance.

2. The method of claim 1, wherein causing a gas to be expelled from the vessel includes delivering a gas from external to the vessel into a head space above the sample.

3. The method of claim 1, wherein causing a gas to be expelled from the vessel includes delivering gas from external to the vessel into the sample.

4. The method of claim 1, wherein causing a gas to be expelled from the vessel includes positioning a gas source within the vessel.

5. The method of claim 1, wherein the sample is a beer or wine precursor.

6. The method of claim 1, wherein the testing tube includes graduations for indicating the length of the medium whose appearance has changed, the length being related to an amount of hydrogen sulfide passed through the tube, the method further including measuring the length using the graduations.

7. The method of claim 6, wherein quantifying the amount of hydrogen sulfide evolved from the sample includes comparing the graduations against the length of the medium whose appearance has changed.

8. The method of claim 1, wherein causing a gas to be expelled from the vessel includes causing a volume of gas which is larger than a volume of the vessel to be expelled from the vessel.

9. The method of claim 8, wherein the volume of gas expelled from the vessel is at least two times the volume of the vessel.

10. The method of claim 8, wherein the volume of gas expelled from the vessel is at least three times the volume of the vessel.

11. The method of claim 1, wherein the reaction is fermentation.

* * * * *